United States Patent
Kennedy et al.

(10) Patent No.: US 12,035,877 B2
(45) Date of Patent: Jul. 16, 2024

(54) ENDOSCOPE INSERTION AND REMOVAL DETECTION SYSTEM

(71) Applicant: Arthrex, Inc., Naples, FL (US)

(72) Inventors: Bruce L. Kennedy, Santa Barbara, CA (US); Larry Higgins, Naples, FL (US); John Batikian, Santa Barbara, CA (US); Wei Yao, Goleta, CA (US); Craig J. Speier, Santa Barbara, CA (US)

(73) Assignee: Arthrex, Inc., Naples, FL (US)

( * ) Notice: Subject to any disclaimer, the term of this patent is extended or adjusted under 35 U.S.C. 154(b) by 1013 days.

(21) Appl. No.: 16/926,075

(22) Filed: Jul. 10, 2020

(65) Prior Publication Data

US 2022/0011724 A1    Jan. 13, 2022

(51) Int. Cl.
*A61B 1/00* (2006.01)
*A61B 1/04* (2006.01)
(Continued)

(52) U.S. Cl.
CPC ...... *A61B 1/00006* (2013.01); *A61B 1/00062* (2013.01); *A61B 1/04* (2013.01);
(Continued)

(58) Field of Classification Search
CPC ............ A61B 1/00006; A61B 1/00009; A61B 1/000096; A61B 1/00002–00004;
(Continued)

(56) References Cited

U.S. PATENT DOCUMENTS

| | | |
|---|---|---|
| 5,836,869 A | 11/1998 | Kudo et al. |
| 6,468,265 B1 | 10/2002 | Evans et al. |

(Continued)

FOREIGN PATENT DOCUMENTS

| | | |
|---|---|---|
| EP | 1993460 | 11/2008 |
| JP | 2005118232 | 5/2005 |

OTHER PUBLICATIONS

Nadeem, Saad, and Arie Kaufman. "Visualization framework for colonoscopy videos." Medical Imaging 2016: Image-Guided Procedures, Robotic Interventions, and Modeling. vol. 9786, International Society for Optics and Photonics, 2016.

(Continued)

*Primary Examiner* — Ryan N Henderson
*Assistant Examiner* — Pamela F Wu
(74) *Attorney, Agent, or Firm* — Greenberg Traurig, LLP; Michael K. Dixon

(57) ABSTRACT

A system for determining elapsed time for a surgical procedure conducted using an endoscope is disclosed. The system may be configured to determine elapsed time for management overseeing operating rooms to determine performance metrics of the operating room such as, but not limited to, operating room consistency and frequency of unusual procedure times to assess operating room efficiency. The system may include determining insertion of an endoscope into a patient and determining removal of the endoscope from a patient. The system may then generate an elapsed surgery time based upon the insertion time of the endoscope into the patient and the removal time of the endoscope from the patient.

18 Claims, 5 Drawing Sheets

(51) Int. Cl.
*G04F 10/00* (2006.01)
*G16H 20/40* (2018.01)
*A61B 1/313* (2006.01)

(52) U.S. Cl.
CPC ............. *G04F 10/00* (2013.01); *G16H 20/40* (2018.01); *A61B 1/00011* (2013.01); *A61B 1/313* (2013.01)

(58) Field of Classification Search
CPC ............ A61B 1/00062; A61B 1/00147; A61B 1/00131; A61B 1/00011; G04F 10/00
USPC .................................. 600/103, 109, 118, 160
See application file for complete search history.

(56) References Cited

U.S. PATENT DOCUMENTS

| | | | |
|---|---|---|---|
| 6,791,601 B1 | 9/2004 | Chang et al. | |
| 6,842,196 B1 | 1/2005 | Swift et al. | |
| 7,232,409 B2 | 6/2007 | Hale et al. | |
| 7,386,147 B2 | 6/2008 | Bodo et al. | |
| 7,577,841 B2 | 8/2009 | Celik | |
| 9,155,592 B2 | 10/2015 | Itkowitz et al. | |
| 9,844,413 B2 | 12/2017 | Daon et al. | |
| 10,105,149 B2 | 10/2018 | Haider et al. | |
| 2006/0100497 A1 | 5/2006 | Sawazaki et al. | |
| 2007/0238981 A1 | 10/2007 | Zhu et al. | |
| 2008/0177136 A1 | 7/2008 | Wang | |
| 2008/0281301 A1 | 11/2008 | Deboer et al. | |
| 2010/0171837 A1 | 7/2010 | Pillman et al. | |
| 2011/0032347 A1 | 2/2011 | Lacey et al. | |
| 2011/0282151 A1 | 11/2011 | Trovato et al. | |
| 2011/0301447 A1 | 12/2011 | Park et al. | |
| 2012/0130160 A1* | 5/2012 | Borrye | A61B 1/04 600/103 |
| 2014/0030669 A1 | 1/2014 | Hey et al. | |
| 2015/0313445 A1 | 11/2015 | Davidson et al. | |
| 2016/0287064 A1 | 10/2016 | Svendsen et al. | |
| 2018/0110398 A1 | 4/2018 | Schwartz et al. | |
| 2019/0290108 A1* | 9/2019 | Nakamitsu | G02B 23/24 |
| 2020/0273581 A1* | 8/2020 | Wolf | A61B 1/000096 |

OTHER PUBLICATIONS

Primus, Manfred Jürgen, Klaus Schoeffmann, and Laszlo Böszörmenyi. "Instrument classification in laparoscopic videos." 2015 13th international workshop on content-based multimedia indexing (CBMI), IEEE, 2015.

Rebello, Keith J. "Applications of MEMS in surgery." Proceedings of the IEEE 92.1 (2004): 43-55.

Willner, Nadav, et al. "Digital Recording and Documentation of Endoscopic Procedures: Do Patients and Doctors Think Alike?." (2016).

World Intellectual Property Organization, "International Search Report and Written Opinion," issued for international patent application No. PCT/US2021/041120.

* cited by examiner

ENDOSCOPE INSERTION AND REMOVAL DETECTION SYSTEM

FIELD OF THE INVENTION

The disclosure relates generally to endoscopic surgical systems, and more particularly, to endoscopic surgical systems configured to measure total elapsed time a surgeon performs a surgical task by monitoring endoscopic insertion into and removal from a patient.

BACKGROUND

In today's push for ever increasing efficiency in medical practices, management teams are seeking to make their medical practices more efficient at every turn. The management teams who oversee operating rooms have attempted to determine the usage efficiency of operating rooms to control costs associated with such use of the operating rooms. Often times, the efficiency of an operating room has been determined by analyzing duration of a complete case, which may include the duration of administering anesthesia to a patient, the duration of joint cleaning prior to probe insertion, the duration of the actual surgery and other events. Analyzing an overall efficiency of an operating room has proven to be difficult and unreliable when the time recorded in connection with operating room usage is comprehensive. Thus, a need exists for a more robust system for analyzing operating room efficiency.

SUMMARY OF THE INVENTION

A system for determining elapsed time for a surgical procedure conducted using an endoscope is disclosed. The system may be configured to determine elapsed time for management overseeing operating rooms to determine performance metrics of the operating room such as, but not limited to, operating room consistency and frequency of unusual procedure times to assess operating room efficiency. The system may include determining insertion of an endoscope into a patient and determining removal of the endoscope from the patient. The system may then generate an elapsed surgery time based upon the insertion time of the endoscope into the patient and the removal time of the endoscope from the patient. The system may communicate the elapsed surgery time via one or more networks.

In an endoscopic minimally invasive surgical procedure, an endoscope may be used to visually access internal body structures through a small incision. The small incision may results in less pain, lower risk of infection, faster recovery and reduce blood loss. The endoscope provides a surgeon with the only view of the surgical site and as such, the surgeon can operate only when the endoscope is inserted into a patient. The system is configured to determine when an endoscope is inserted into and removed from a patient to then determine the elapsed time for a surgical procedure. The system may use several sources of information that can be gathered to indicate when an endoscope is inserted into and removed from a patient. These sources include an initial white balance step as start of case qualifier, auto exposure status by continued monitoring and image analysis using image processing during these events to provide additional accuracy. Both of these events are expected to occur repeatedly during a medical procedure on a patient as an endoscope is moved between portals and cleaned. During a medical procedure, a camera attached the distal end of the endoscope undergoes adjustments gain and exposure time as well as illumination level to deliver the best image to the surgeon. As the endoscope is inserted into a patient, a unique signature of these parameters is used to identify the insertion of the endoscope into the patient.

The system for determining elapsed time for a surgical procedure conducted using an endoscope may include a memory that stores instructions and a processor that executes the instructions to perform operations. The operations may include determining an insertion time of an endoscope inserted into a patient via monitoring camera parameters of a camera that is positioned within a distal end of the endoscope to identify the insertion time of the endoscope into the patient. The operations may also include determining a removal time of the endoscope from a patient via monitoring camera parameters to identify the removal time of the endoscope from the patient. The operations may also include generating an elapsed surgery time based upon the insertion time of the endoscope into the patient and the removal time of the endoscope from the patient.

The operation of monitoring camera parameters to identify the insertion time of the endoscope into the patient may include comprises monitoring a rate of change of a camera exposure index to identify a point in time in which the endoscope is inserted into the patient. Monitoring a rate of change of a camera exposure index may include monitoring a rate of change of a camera exposure index formed from a combination of exposure time and signal gain.

The operation of monitoring camera parameters to identify the removal time of the endoscope into the patient may include monitoring a rate of change of a camera exposure index to identify a point in time in which the endoscope is removed from the patient. The operation of monitoring a rate of change of a camera exposure index may include monitoring a rate of change of a camera exposure index formed from a combination of exposure time and signal gain.

The system may also be configured to account for potential false signals. Capturing a still image affects the exposure index in a way similar to an endoscope insertion. False triggers of this sort can be rejected because the system is aware of the image capture events and can mute the endoscope insertion and removal. For example, the system may operate such that the operations include receiving indication of still image capture events within the camera and ignoring a camera exposure index associated with the camera during still image capture events to prevent false identification of insertion of the endoscope from the patient. In addition, the system may also operate such that the operations include receiving indication of still image capture events within the camera and ignoring a camera exposure index associated with the camera during still image capture events to prevent false identification of removal of the endoscope from the patient.

The system may also be configured to further refine the analysis of the camera parameters monitored. For example, and not by way of limitation, the system may be configured to identify elements associated with each peak, namely, a time width of each peak which provides a unique characteristic of the peak and a logical order to the peak. The system may also be configured such that the period of time between events can be analyzed to identify a signature that reveals which event has occurred. The system may also analyze the duration of events to determine which event has occurred. The system may analyze the logical sequence of events to determine insertion and removal events. The system may be configured to identify events such as, but not limited to, "case start", "image capture" and "white balance" to assist in the identification of endoscope insertion and endoscope removal events. The system may also be configured to filter out multiple peaks occurring repeatedly in a short duration of time to prevent incorrect identification of insertion and removal events.

An advantage of the system for determining elapsed time for a surgical procedure conducted using an endoscope is that the system is able to determine the time spent when a surgeon is actually working on a patient rather than an aggregate time of when a patient is in an operating but other ancillary activities are occurring.

These and other embodiments are described in more detail below.

DETAILED DESCRIPTION OF THE FIGURES

As shown in FIGS. 1-6, a system 10 for determining elapsed time for a surgical procedure conducted using an endoscope 12 is disclosed. The system 10 may be configured to determine elapsed time for management overseeing operating rooms to determine performance metrics of the operating room such as, but not limited to, operating room consistency and frequency of unusual procedure times to assess operating room efficiency. The system 10 may include determining insertion of an endoscope 12 into a patient 14 and determining removal of the endoscope 12 from the patient 14. The system 10 may then generate an elapsed surgery time based upon the insertion time of the endoscope 12 into the patient 14 and the removal time of the endoscope 12 from the patient 14. The system 10 may communicate the elapsed surgery time via one or more networks 24.

Figure 4:
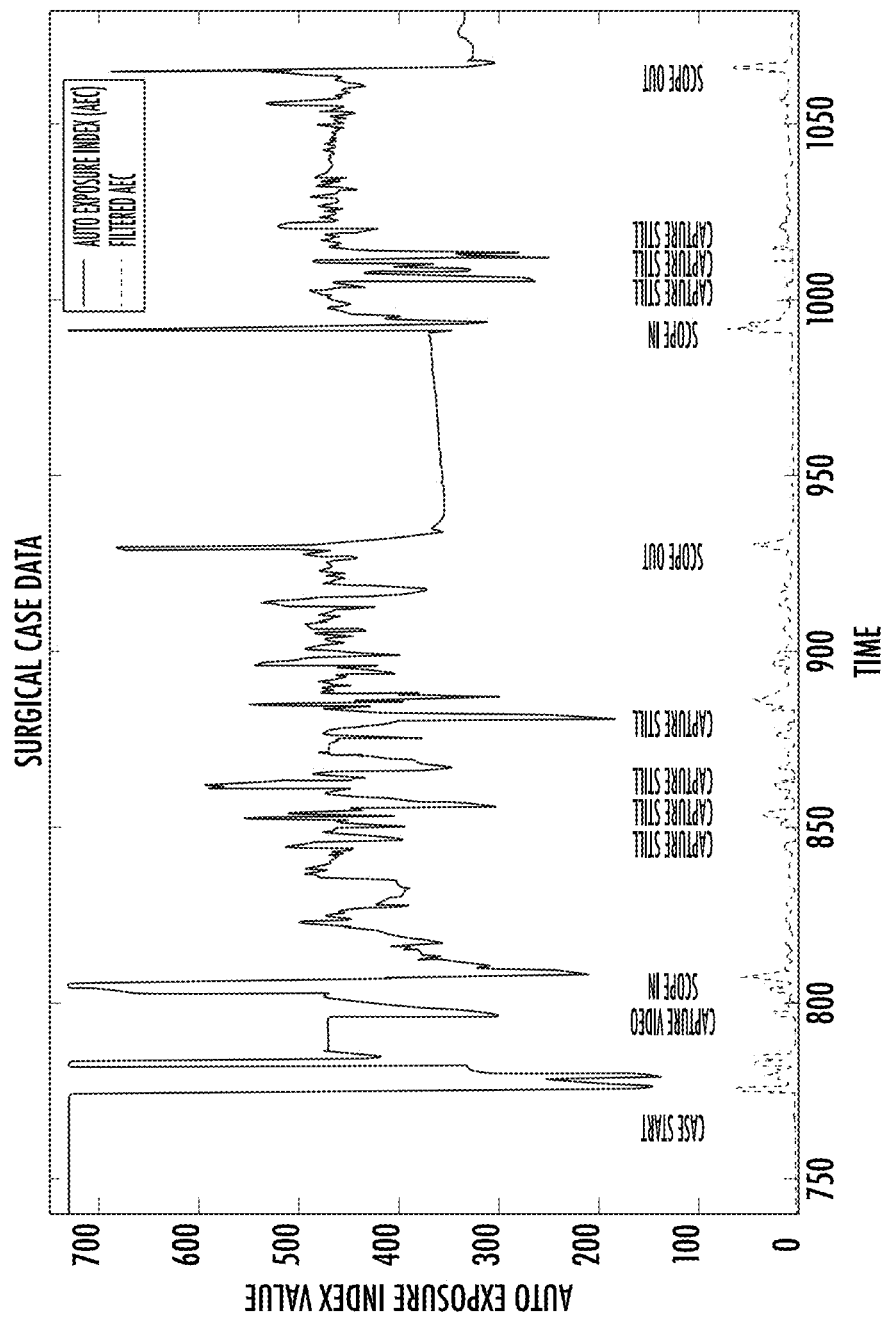
FIG. 4 is a graph of camera auto exposure index relative to time as an endoscope is inserted into a patient, still images are captured a multiple points in time and the endoscope is removed from the patient.
Figure 5:
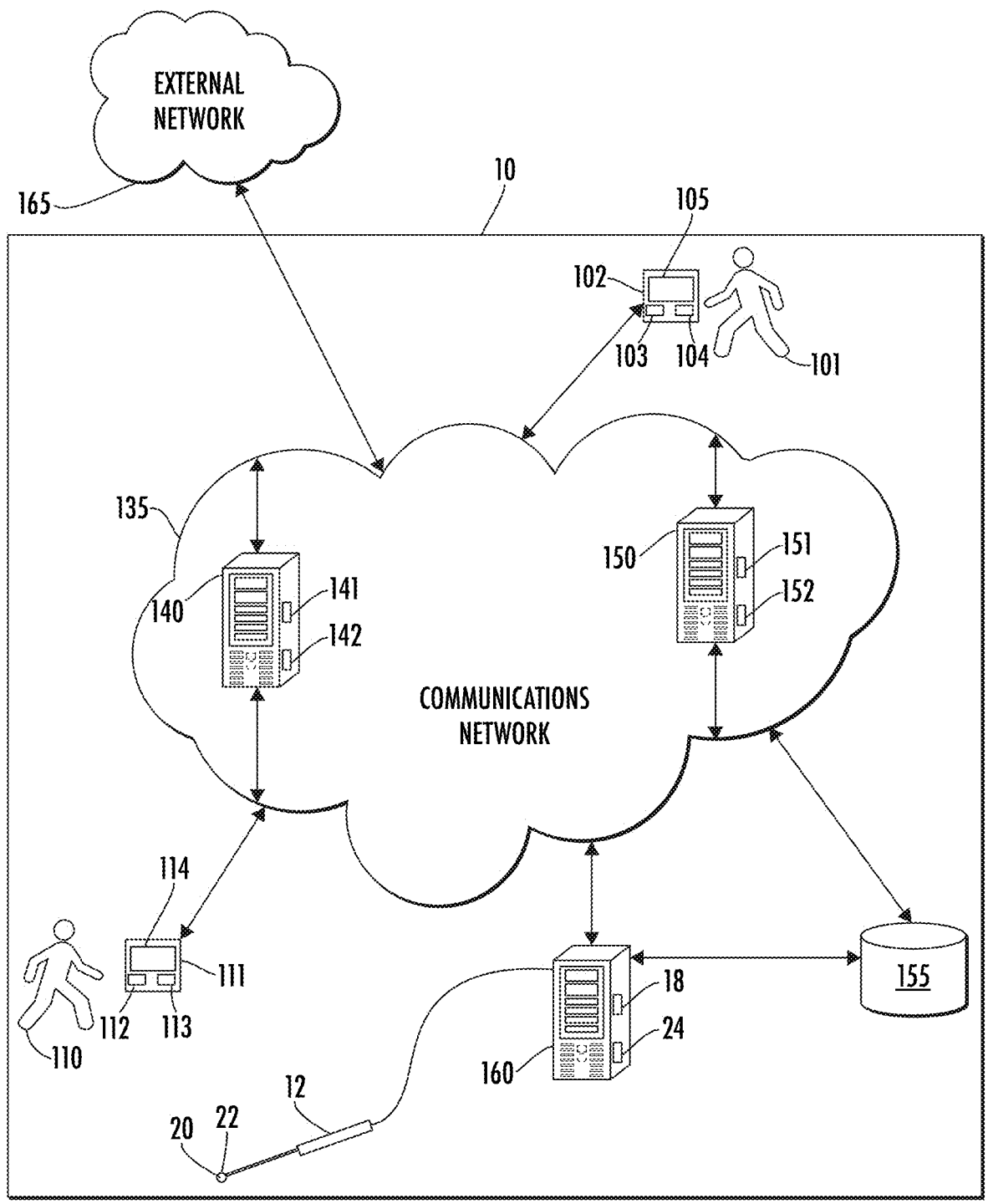
FIG. 5 is a schematic diagram of the system for determining elapsed time for a surgical procedure conducted using an endoscope including a communications network enabling users to access data collected via the system from remote locations.

In an endoscopic minimally invasive surgical procedure, an endoscope 12 may be used to visually access internal body structures through a small incision. The small incision may results in less pain, lower risk of infection, faster recovery and reduce blood loss. The endoscope provides a surgeon with the only view of the surgical site and as such, the surgeon can operate only when the endoscope is inserted into a patient 14. The system 10 is configured to determine when an endoscope 12 is inserted into and removed from a patient 14 to then determine the elapsed time for a surgical procedure. The system 10 may use several sources of information that can be gathered to indicate when an endoscope 12 is inserted into and removed from a patient 14. These sources include an initial white balance step as start of case qualifier, auto exposure status by continued monitoring and image analysis using image processing during these events to provide additional accuracy. Both of these events are expected to occur repeatedly during a medical procedure on a patient 14 as an endoscope 12 is moved between portals and cleaned. During a medical procedure, as shown in FIG. 4, a camera 20 attached the distal end 22 of the endoscope 12 undergoes adjustments gain and exposure time as well as illumination level to deliver the best image to the surgeon. As the endoscope 12 is inserted into a patient 14, a unique signature of these parameters is used to identify the insertion of the endoscope 12 into the patient 14.

The system 10 for determining elapsed time for a surgical procedure conducted using an endoscope 12 may include a memory 18 that stores instructions and a processor 24 that executes the instructions to perform operations. The memory 18 and processor 24 may be contained within a server 160 that maybe in communication with a communications network 135 enabling users to access the data in remote locations via other devices. The operations may include determining an insertion time of an endoscope 12 inserted into a patient 14 via monitoring camera parameters of a camera 20 that is positioned within a distal end 22 of the endoscope 12 to identify the insertion time of the endoscope 12 into the patient 14. The operations may also include determining a removal time of the endoscope 12 from a patient 14 via monitoring camera parameters to identify the removal time of the endoscope 12 from the patient 14. The operations may also include generating an elapsed surgery time based upon the insertion time of the endoscope 12 into the patient 14 and the removal time of the endoscope 12 from the patient 14.

Figure 3:
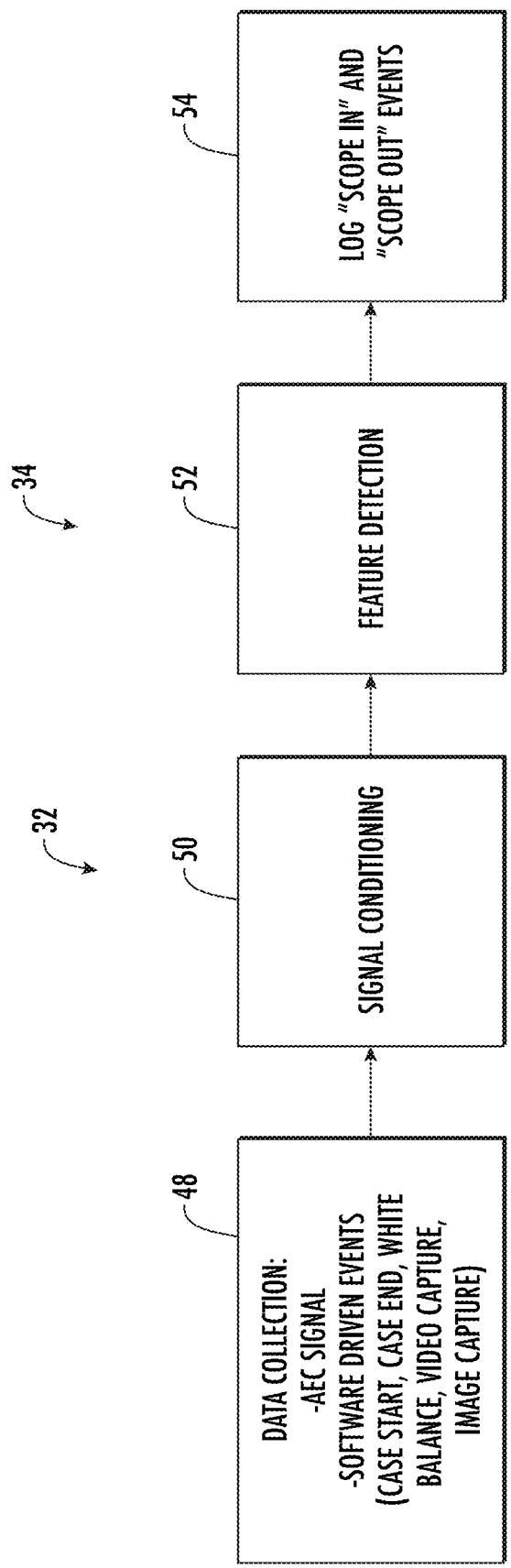
FIG. 3 is a flow diagram of detailed steps of a portion of a method for determining elapsed time for a surgical procedure conducted using an endoscope shown in FIG. 2.

The system 10 may determine an insertion time of an endoscope 12 inserted into a patient 14 via monitoring camera parameters of a camera 20 by, in at least one embodiment, monitoring an automatic exposure control (AEC) signal. The system 10 may at step 48 collect data via monitoring AEC signals and monitoring software driven events, such as, but not limited to, case start, case end, white balance, video capture and image capture. As shown in FIG. 3, the system 10 may include signal conditioning at step 50 to enable the system 10 to detect the targeted feature events. The system 10 may include feature detection at step 52. Once the system 10 has detected a target feature, the system 10 may save events at step 54 such as when an endoscope 12 is inserted in a patient 14, referred to as a Scope In event, and when an endoscope 12 is removed from a patient 14, referred to as a Scope Out event.

The operation of monitoring camera parameters to identify the insertion time of the endoscope 12 into the patient 14 may include comprises monitoring a rate of change of a camera exposure index, as shown in FIG. 4, to identify a point in time in which the endoscope 12 is inserted into the patient 14. Monitoring a rate of change of a camera exposure index may include monitoring a rate of change of a camera exposure index formed from a combination of exposure time and signal gain.

The operation of monitoring camera parameters to identify the removal time of the endoscope 12 into the patient 14 may include monitoring a rate of change of a camera exposure index to identify a point in time in which the endoscope 12 is removed from the patient 14. The operation of monitoring a rate of change of a camera exposure index may include monitoring a rate of change of a camera exposure index formed from a combination of exposure time and signal gain.

The system 10 may also be configured to account for potential false signals. Capturing a still image affects the exposure index in a way similar to an endoscope insertion. False triggers of this sort can be rejected because the system 10 is aware of the image capture events and can mute the endoscope insertion and removal. For example, the system 10 may operate such that the operations include receiving indication of still image capture events within the camera 20 and ignoring a camera exposure index associated with the camera 20 during still image capture events to prevent false identification of insertion of the endoscope 12 from the patient 14. In addition, the system may also operate such that the operations include receiving indication of still image capture events within the camera 20 and ignoring a camera exposure index associated with the camera during still image capture events to prevent false identification of removal of the endoscope 12 from the patient 14.

Figure 1:
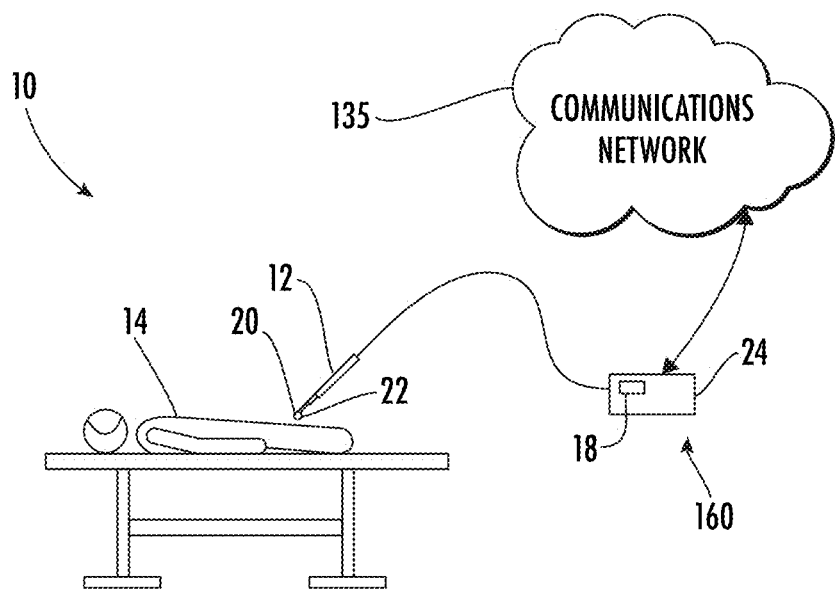
FIG. 1 is a schematic diagram of a system for determining elapsed time for a surgical procedure conducted using an endoscope.
Figure 2:
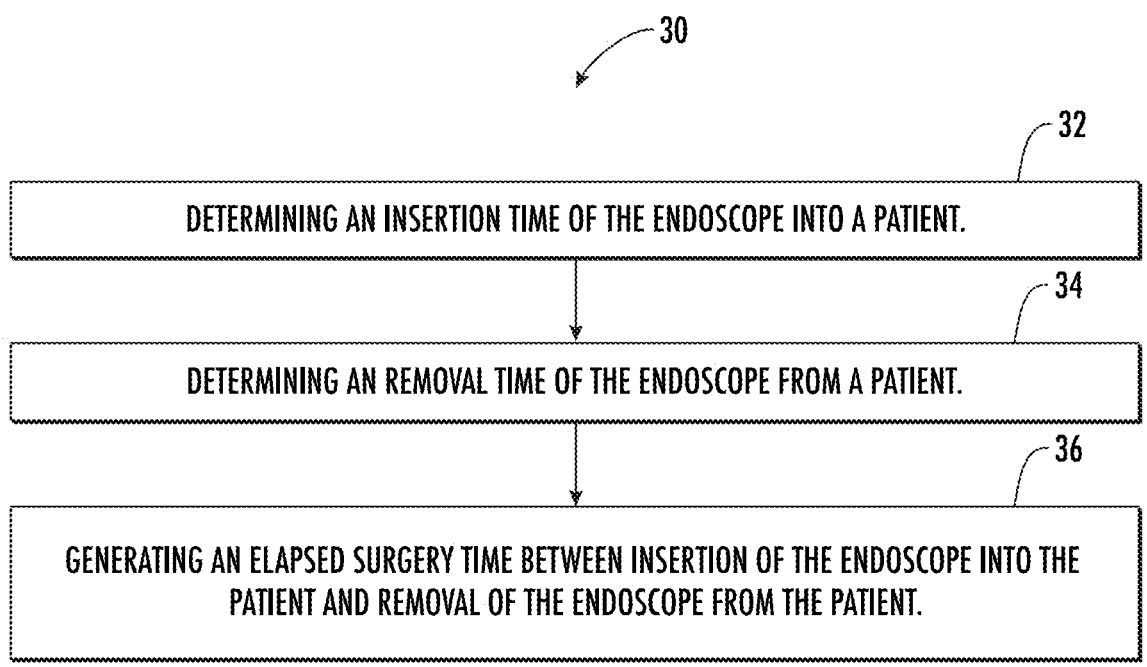
FIG. 2 is a flow diagram of a method for determining elapsed time for a surgical procedure conducted using an endoscope.

As shown in FIG. 2, a method 30 for determining elapsed time for a surgical procedure conducted using an endoscope 12 is disclosed. The method 30 may include at step 32 determining an insertion time of an endoscope 12 into a patient 14 via monitoring camera parameters of the camera 20 that is positioned within a distal end 22 of the endoscope 12 to identify the insertion time of the endoscope 12 into the patient 14. The method of performing step 32 may be according to the steps 48-54 of FIG. 3. The method 30 may also include at step 34 determining a removal time of the endoscope 12 from a patient 14 via monitoring camera parameters to identify the removal time of the endoscope 12 from the patient 14. The method of performing step 34 may be according to the steps 48-54 of FIG. 3. The method 30 may also include at step 36 generating an elapsed surgery time based upon the insertion time of the endoscope 12 into the patient 14 and the removal time of the endoscope 12 from the patient 14.

The step 32 of determining an insertion time of an endoscope 12 into a patient 14 via monitoring camera parameters of the camera 20 to identify the insertion time of the endoscope 12 into the patient 14 may include monitoring a rate of change of a camera exposure index to identify a point in time in which the endoscope 12 is inserted into a patient 14. The step 32 including monitoring a rate of change of a camera exposure index may include monitoring a rate of change of a camera exposure index formed from a combination of exposure time and signal gain of the camera.

The method 30 may also include receiving indication of still image capture events within the camera 20 and ignoring a camera exposure index associated with the camera 20 during still image capture events to prevent false identification of insertion of the endoscope 12 from the patient 14.

The step 34 of determining a removal time of an endoscope 12 into a patient 14 via monitoring camera parameters of the camera 20 to identify the insertion time of the endoscope 12 into the patient 14 may include monitoring a rate of change of a camera exposure index to identify a point in time in which the endoscope 12 is removed from the patient 14. The step 32 including monitoring a rate of change of a camera exposure index may include monitoring a rate of change of a camera exposure index formed from a combination of exposure time and signal gain.

The method 30 may also include at step 38 receiving indication of still image capture events within the camera 20 and ignoring a camera exposure index associated with the camera 20 during still image capture events to prevent false identification of removal of the endoscope 12 from the patient 14.

The system 10 may also be configured to further refine the analysis of the camera parameters monitored. In particular, the system 10 may be configured to determine when events, such as endoscope insertion or endoscope removal, have occurred using logical analysis of data or by using time in conjunction with camera parameters previously set forth. For example, and not by way of limitation, the system 10 may be configured at step 36 to identify elements associated with each peak, namely, a time width of each peak which provides a unique characteristic of the peak and a logical order to the peak. The system 10 may also be configured such that the period of time between events can be identified at step 36 to determine a signature that reveals which event has occurred. The system 10 may also analyze at step 36 the duration of events to determine which event has occurred. The system 10 may be preprogrammed with typical duration of events, such as, but not limited to, "case start", "image capture", "white balance" and "case end". The system 10 may analyze the logical sequence of events to determine insertion and removal events. The system 10 may be configured to identify events such as, but not limited to, "case start", "image capture", "white balance" and "case end" to assist in the identification of endoscope insertion and endoscope removal events and to ignore false signals. The system 10 may also be configured to filter out multiple peaks occurring repeatedly in a short duration of time to prevent incorrect identification of insertion and removal events.

The system 10 may also be configured to include a non-transitory computer-readable device 1022 comprising instructions, which when loaded and executed by a processor 1002, cause the processor 1002 to perform operations including the step 32 of determining an insertion time of an endoscope 12 into the patient 14 via monitoring camera parameters of the camera 20 that is positioned within a distal end 22 of the endoscope 12 to identify the insertion time of the endoscope 12 into the patient 14. The non-transitory computer-readable device 1022 may also include instructions which cause the processor 1002 to perform operations including the step 34 of determining a removal time of the endoscope 12 from a patient 14 via monitoring camera parameters to identify the removal time of the endoscope 12 from the patient 14. The non-transitory computer-readable device 1022 may also include instructions which cause the processor 1002 to perform operations including the step 36 of generating an elapsed surgery time based upon the insertion time of the endoscope 12 into the patient 14 and the removal time of the endoscope 12 from the patient 14.

As shown in FIGS. 1-6, systems 10 and methods 30 for determining elapsed time for a surgical procedure conducted using an endoscope 12 are disclosed. The system 10 may be configured to enable users to access information on the system 10 via computing devices remote from an operating room. As such, diagnostics and review of the data may take place anywhere desired. The system 10 may be configured to support, but is not limited to supporting, machine learning services, data and content services, computing applications and services, cloud computing services, internet services, satellite services, telephone services, software as a service (SaaS) applications and services, mobile applications and services, platform as a service (PaaS) applications and services, web services, client servers, and any other computing applications and services. The system 10 may include a first user 101, who may utilize a first user device 102 to access data, content, and applications, or to perform a variety of other tasks and functions. As an example, the first user 101 may utilize first user device 102 to access an application (e.g. a browser or a mobile application) executing on the first user device 102 that may be utilized to access web pages, data, and content associated with the system 10. The system 10 may include any number of users.

The first user device 102 utilized by the first user 101 may include a memory 103 that includes instructions, and a processor 104 that executes the instructions from the memory 103 to perform the various operations that are performed by the first user device 102. In certain embodiments, the processor 104 may be hardware, software, or a combination thereof. The first user device 102 may also include an interface 105 (e.g. screen, monitor, graphical user interface, etc.) that may enable the first user 101 to interact with various applications executing on the first user device 102, to interact with various applications executing within the system 10, and to interact with the system 10 itself. In certain embodiments, the first user device 102 may include components that provide non-visual outputs. For example, the first user device 102 may include speakers, haptic components, tactile components, or other components, which may be utilized to generate non-visual outputs that may be perceived and/or experienced by the first user 101. In certain embodiments, the first user device 102 may be configured to not include interface 105. In certain embodiments, the first user device 102 may be a computer, a laptop, a tablet device, a phablet, a server, a mobile device, a smartphone, a smart watch, and/or any other type of computing device. Illustratively, the first user device 102 is shown as a mobile device in FIG. 1. The first user device 102 may also include a global positioning system (GPS), which may include a GPS receiver and any other necessary components for enabling GPS functionality, accelerometers, gyroscopes, sensors, and any other componentry suitable for a mobile device.

In addition to the first user 101, the system 10 may include a second user 110, who may utilize a second user device 111 to access data, content, and applications, or to perform a variety of other tasks and functions. As with the first user 101, in certain embodiments, the second user 110 may be any type of user that may review data from the camera 20, total elapsed time of use of an endoscope in a patient, or other relevant data. Much like the first user 101, the second user 110 may utilize second user device 111 to access an application (e.g. a browser or a mobile application) executing on the second user device 111 that may be utilized to access web pages, data, and content associated with the system 10. The second user device 111 may include a memory 112 that includes instructions, and a processor 113 that executes the instructions from the memory 112 to perform the various operations that are performed by the second user device 111. In certain embodiments, the processor 113 may be hardware, software, or a combination thereof. The second user device 111 may also include an interface 114 (e.g. a screen, a monitor, a graphical user interface, etc.) that may enable the second user 110 to interact with various applications executing on the second user device 111, to interact with various applications executing in the system 10, and to interact with the system 10. In certain embodiments, the second user device 111 may be a computer, a laptop, a tablet device, a phablet, a server, a mobile device, a smartphone, a smart watch, and/or any other type of computing device. Illustratively, the second user device 111 may be a computing device in FIG. 1. The second user device 111 may also include any of the componentry described for first user device 102.

In certain embodiments, the first user device 102 and the second user device 111 may have any number of software applications and/or application services stored and/or accessible thereon. For example, the first and second user devices 102, 111 may include artificial intelligence-based applications, machine learning-based applications, applications for facilitating the completion of tasks, cloud-based applications, search engine applications, natural language processing applications, database applications, algorithmic applications, phone-based applications, product-ordering applications, business applications, e-commerce applications, media streaming applications, content-based applications, database applications, gaming applications, internet-based applications, browser applications, mobile applications, service-based applications, productivity applications, video applications, music applications, social media applications, presentation applications, any other type of applications, any types of application services, or a combination thereof. In certain embodiments, the software applications and services may include one or more graphical user interfaces so as to enable the first and second users 101, 110 to readily interact with the software applications. The software applications and services may also be utilized by the first and second users 101, 110 to interact with any device in the system 10, any network in the system 10, or any combination thereof. For example, the software applications executing on the first and second user devices 102, 111 may be applications for receiving data, applications for storing data, applications for receiving demographic and preference information, applications for transforming data, applications for executing mathematical algorithms, applications for generating and transmitting electronic messages, applications for generating and transmitting various types of content, any other type of applications, or a combination thereof. In certain embodiments, the first and second user devices 102, 111 may include associated telephone numbers, internet protocol addresses, device identities, or any other identifiers to uniquely identify the first and second user devices 102, 111 and/or the first and second users 101, 110. In certain embodiments, location information corresponding to the first and second user devices 102, 111 may be obtained based on the internet protocol addresses, by receiving a signal from the first and second user devices 102, 111, or based on profile information corresponding to the first and second user devices 102, 111. In certain embodiments, the location information may be obtained by utilizing global positioning systems of the first and/or second user devices 102, 111.

The system 10 may also include a communications network 135. The communications network 135 of the system 10 may be configured to link each of the devices in the system 10 to one another. For example, the communications network 135 may be utilized by the first user device 102 to connect with other devices within or outside communications network 135. Additionally, the communications network 135 may be configured to transmit, generate, and receive any information and data traversing the system 10. In certain embodiments, the communications network 135 may include any number of servers, databases, or other componentry, and may be controlled by a service provider. The communications network 135 may also include and be connected to a cloud-computing network, a phone network, a wireless network, an Ethernet network, a satellite network, a broadband network, a cellular network, a private network, a cable network, the Internet, an internet protocol network, a content distribution network, a virtual private network, any network, or any combination thereof. Illustratively, server 140 and server 150 are shown as being included within communications network 135.

Notably, the functionality of the system 10 may be supported and executed by using any combination of the servers 140, 150, and 160. The servers 140, and 150 may reside in communications network 135, however, in certain embodiments, the servers 140, 150 may reside outside communications network 135. The servers 140 and 150 may be utilized to perform the various operations and functions provided by the system 10, such as those requested by applications executing on the first and second user devices 102, 111. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 150 may include a memory 151 that includes instructions, and a processor 152 that executes the instructions from the memory 151 to perform the various operations that are performed by the server 150. In certain embodiments, the servers 140, 150, and 160 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 140, 150 may be communicatively linked to the communications network 135, any network, any device in the system 10, or any combination thereof.

The database 155 of the system 10 may be utilized to store and relay information that traverses the system 10, cache information and/or content that traverses the system 10, store data about each of the devices in the system 10, and perform any other typical functions of a database. In certain embodiments, the database 155 may store the output from any operation performed by the system 10, operations performed and output generated by the first and second user devices 102, 111, the servers 140, 150, 160, or any combination thereof. In certain embodiments, the database 155 may store a record of any and all information obtained from any data sources utilized by the system 10 to facilitate the operative functions of the system 10 and its components, store any information and data obtained from the internal and external data sources 201, 202, store the agglomerated models 208, store outputs generated by an application under evaluation 230, store feedback received from the first and second users 101, 110 and/or the first and second user devices 102, 111, store inputs entered into or utilized to interact with the application under evaluation 230, store software code 245 generated by the system 10, store reports 242 generated by the system 10, store analyses 243 generated by the system 10, store test results 246 generated by the system 10, store test data 247, store media training videos and media content, store any information generated and/or received by the system 10, any other data traversing the system 10, or any combination thereof. In certain embodiments, the database 155 may be connected to or reside within the communications network 135, any other network, or a combination thereof. In certain embodiments, the database 155 may serve as a central repository for any information associated with any of the devices and information associated with the system 10. Furthermore, the database 155 may include a processor and memory or be connected to a processor and memory to perform the various operations associated with the database 155. In certain embodiments, the database 155 may be connected to the servers 140, 150, 160, the first user device 102, the second user device 111, any devices in the system 10, any other device, any network, or any combination thereof.

The database 155 may also store information obtained from the system 10, store information associated with the first and second users 101, 110, store location information for the first and second user devices 102, 111 and/or first and second users 101, 110, store user profiles associated with the first and second users 101, 110, store device profiles associated with any device in the system 10, store communications traversing the system 10, store user preferences, store demographic information for the first and second users 101, 110, store information associated with any device or signal in the system 10, store information relating to usage of applications accessed by the first and second user devices 102, 111, store any information obtained from any of the networks in the system 10, store historical data associated with the first and second users 101, 110, store device characteristics, store information relating to any devices associated with the first and second users 101, 110, or any combination thereof. The user profiles may include any type of information associated with an individual (e.g. first user 101 and/or second user 110), such as, but not limited to a username, a password, contact information, demographic information, psychographic information, an identification of applications used or associated with the individual, any attributes of the individual, any other information, or a combination thereof. Device profiles may include any type of information associated with a device, such as, but not limited to, operating system information, hardware specifications, information about each component of the device (e.g. sensors, processors, memories, batteries, etc.), attributes of the device, any other information, or a combination thereof.

In certain embodiments, the database 155 may store algorithms facilitating the operation of the system 10 itself, any software application utilized by the system 10, or any combination thereof. In certain embodiments, the database 155 may be configured to store any information generated and/or processed by the system 10, store any of the information disclosed for any of the operations and functions disclosed for the system 10 herewith, store any information traversing the system 10, or any combination thereof. Furthermore, the database 155 may be configured to process queries sent to it by any device in the system 10.

In certain embodiments, the system 10 may communicate and/or interact with an external network 165. In certain embodiments, the external network 165 may include any number of servers, databases, or other componentry, and, in certain embodiments, may be controlled by a service provider. The external network 165 may also include and be connected to a cloud-computing network, a phone network, a wireless network, an Ethernet network, a satellite network, a broadband network, a cellular network, a private network, a cable network, the Internet, an internet protocol network, a content distribution network, a virtual private network, any network, or any combination thereof.

The system 10 may also include a software application or program, which may be configured to perform and support the operative functions of the system 10. In certain embodiments, the application may be a software program, a website, a mobile application, a software application, a software process, or a combination thereof, which may be made accessible to users utilizing one or more computing devices, such as first user device 102 and second user device 111. The application of the system 10 may be accessible via an internet connection established with a browser program executing on the first or second user devices 102, 111, a mobile application executing on the first or second user devices 102, 111, or through other suitable means. Additionally, the application may allow users and computing devices to create accounts with the application and sign-in to the created accounts with authenticating username and password log-in combinations. In certain embodiments, the software application may execute directly as an installed program on the first and/or second user devices 102, 111, such as a mobile application or a desktop application. In certain embodiments, the software application may execute directly on any combination of the servers 140, 150, 160.

The software application may include multiple programs and/or functions that execute within the software application and/or are accessible by the software application. For example, the software application may include an application that generates web content and pages that may be accessible to the first and/or second user devices 102, 111, any type of program, or any combination thereof.

The systems and methods disclosed herein may include further functionality and features. For example, the operative functions of the system 10 and methods 30 may be configured to execute on a special-purpose processor specifically configured to carry out the operations provided by the system 10 and methods 30. Notably, the operative features and functionality provided by the system 10 and methods 30 may increase the efficiency of computing devices that are being utilized to facilitate the functionality provided by the system 10 and methods 30. For example, the system 10 and methods 30 can optimize the performance of future actions through machine learning, such that a reduced amount of computer operations need to be performed by the devices in the system 10 using the processors and memories of the system 10 than in systems that are not capable of machine learning as described in this disclosure. In such a context, less processing power may need to be utilized because the processors and memories do not need to perform actions, operations, and analyses that have already been conducted by the system 10. In certain embodiments, the system 10 may learn that certain state(s) associated with and/or from discovery and/or testing may be faster on certain processing hardware. For example, for a state with complex mathematical operations and/or graphics, the system 10 may perform better when there is a floating point processor or a graphics processing unit. As a result, the functionality provided by the system 10 and methods 30 may provide substantial savings in the usage of computer resources by utilizing the software and functionality provided in the present disclosure.

Notably, in certain embodiments, various functions and features of the system 10 and methods may operate without human intervention and may be conducted entirely by computing devices, robots, programs, and/or processes. For example, in certain embodiments, multiple computing devices may interact with devices of the system 10 to provide the functionality supported by the system 10. Additionally, in certain embodiments, system 10 may operate continuously to reduce the possibility of defects, conflicts, and/or errors from being introduced into the system 10. In certain embodiments, the system 10 and method may also provide effective computing resource management by utilizing the features and functions described in the present disclosure. For example, in certain embodiments, the system 10 may specify a quantity of computer processor resources (e.g. processor clock cycles, processor speed, processor cache, etc.) that may be dedicated to obtaining data from the camera 20. For example, the system 10 may indicate a quantity of processor cycles of a processor that may be utilized to obtain data, process obtained data, and/or specify a selected amount of processing power that may be dedicated to obtaining and processing data from the camera 20.

In certain embodiments, any device or program in the system 10 may transmit a signal to a memory device to cause the memory device to only dedicate a selected amount of memory resources to the various operations of the system 10. In certain embodiments, the system 10 and methods may also include transmitting signals to processors and memories to only perform the operative functions of the system 10 and methods 30 at time periods when usage of processing resources and/or memory resources in the system 10 is at a selected and/or threshold value. In certain embodiments, the system 10 and methods may include transmitting signals to the memory devices utilized in the system 10, which indicate which specific portions (e.g. memory sectors, etc.) of the memory should be utilized to store any of the data utilized or generated by the system 10. Notably, the signals transmitted to the processors and memories may be utilized to optimize the usage of computing resources while executing the operations conducted by the system 10. As a result, such features provide substantial operational efficiencies and improvements over existing technologies.

Figure 6:
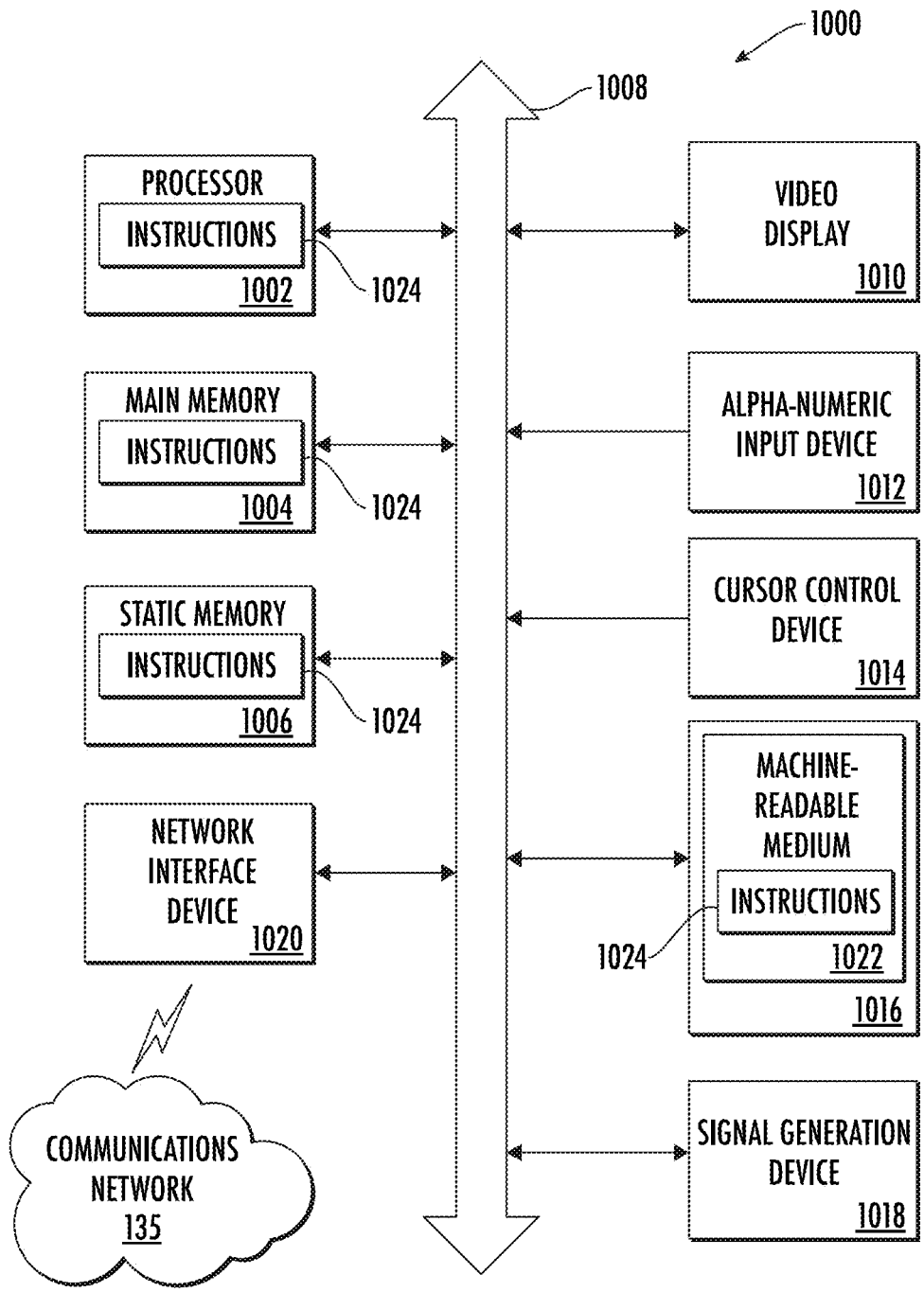
FIG. 6 is a schematic diagram of a machine in the form of a computer system within which a set of instructions, when executed, may cause the machine to perform any one or more of the methodologies or operations of the systems and methods for autonomously testing a computing system.

Referring now also to FIG. 6, at least a portion of the methodologies and techniques described with respect to the exemplary embodiments of the system 10 can incorporate a machine, such as, but not limited to, computer system 1000, or other computing device within which a set of instructions, when executed, may cause the machine to perform any one or more of the methodologies or functions discussed above. The machine may be configured to facilitate various operations conducted by the system 10. For example, the machine may be configured to, but is not limited to, assist the system 10 by providing processing power to assist with processing loads experienced in the system 10, by providing storage capacity for storing instructions or data traversing the system 10, or by assisting with any other operations conducted by or within the system 10.

In some embodiments, the machine may operate as a standalone device. In some embodiments, the machine may be connected (e.g., using communications network 135, another network, or a combination thereof) to and assist with operations performed by other machines and systems, such as, but not limited to, the first user device 102, the second user device 111, the server 140, the server 150, the database 155, the server 160, or any combination thereof. The machine may assist with operations performed by other component in the system, any programs in the system, or any combination thereof. The machine may be connected with any component in the system 10. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 1000 may include a processor 1002 (e.g., a central processing unit (CPU), a graphics processing unit (GPU, or both), a main memory 1004 and a static memory 1006, which communicate with each other via a bus 1008. The computer system 100 may further include a video display unit 1010, which may be, but is not limited to, a liquid crystal display (LCD), a flat panel, a solid state display, or a cathode ray tube (CRT). The computer system 100 may include an input device 1012, such as, but not limited to, a keyboard, a cursor control device 1014, such as, but not limited to, a mouse, a disk drive unit 1016, a signal generation device 1018, such as, but not limited to, a speaker or remote control, and a network interface device 1020.

The disk drive unit 1016 may include a machine-readable medium 1022 on which is stored one or more sets of instructions 1024, such as, but not limited to, software embodying any one or more of the methodologies or functions described herein, including those methods illustrated above. The instructions 1024 may also reside, completely or at least partially, within the main memory 1004, the static memory 1006, or within the processor 1002, or a combination thereof, during execution thereof by the computer system 100. The main memory 1004 and the processor 1002 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations may include, but are not limited to, distributed processing or component/object distributed processing, parallel processing, or virtual machine processing can also be constructed to implement the methods described herein.

The present disclosure contemplates a machine-readable medium 1022 containing instructions 1024 so that a device connected to the communications network 135, another network, or a combination thereof, can send or receive voice, video or data, and communicate over the communications network 135, another network, or a combination thereof, using the instructions. The instructions 1024 may further be transmitted or received over the communications network 135, another network, or a combination thereof, via the network interface device 1020.

While the machine-readable medium 1022 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other rewritable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. A system for determining elapsed time for a surgical procedure conducted using an endoscope, comprising:
   a memory that stores instructions; and
   a processor that executes the instructions to perform operations, the operations comprising:
      determining an insertion time of an endoscope inserted into a patient via monitoring camera parameters of a camera that is positioned within the endoscope to identify the insertion time of the endoscope into the patient;
      determining a removal time of the endoscope from the patient via monitoring camera parameters to identify the removal time of the endoscope from the patient;
      generating an elapsed surgery time based upon the insertion time of the endoscope into the patient and the removal time of the endoscope from the patient; and
      wherein the operation of monitoring camera parameters to identify the insertion time of the endoscope into the patient comprises monitoring a rate of change of a camera exposure index to identify a point in time in which the endoscope is inserted into the patient.

2. The system of claim 1, wherein the operation of monitoring the rate of change of the camera exposure index comprises monitoring a rate of change of a camera exposure index formed from a combination of exposure time and signal gain.

3. The system of claim 1, wherein the operations further comprise receiving indication of still image capture events within the camera and ignoring the camera exposure index associated with the camera during still image capture events to prevent false identification of insertion of the endoscope from the patient.

4. The system of claim 1, wherein generating the elapsed surgery time comprises determining a period of time between endoscopic events to determine a signature of at least one camera parameter that reveals which event has occurred.

5. The system of claim 1, wherein generating the elapsed surgery time comprises identifying elements associated with a peak in a waveform representing at least one camera parameter including a time width for the peak which provides a unique characteristic of the peak and a logical order to the peak.

6. The system of claim 1, wherein generating the elapsed surgery time comprises analyzing a duration of events to determine which event has occurred.

7. The system of claim 1, wherein generating the elapsed surgery time comprises identifying a logical sequence of events to determine insertion and removal events.

8. The system of claim 1, wherein generating the elapsed surgery time comprises filtering out multiple peaks in a waveform representing at least one camera parameter occurring repeatedly in a short duration of time to prevent incorrect identification of insertion and removal events.

9. A system for determining elapsed time for a surgical procedure conducted using an endoscope, comprising:
a memory that stores instructions; and
a processor that executes the instructions to perform operations, the operations comprising:
determining an insertion time of an endoscope inserted into a patient via monitoring camera parameters of a camera that is positioned within the endoscope to identify the insertion time of the endoscope into the patient;
determining a removal time of the endoscope from the patient via monitoring camera parameters to identify the removal time of the endoscope from the patient;
generating an elapsed surgery time based upon the insertion time of the endoscope into the patient and the removal time of the endoscope from the patient; and
wherein the operation of monitoring camera parameters to identify the removal time of the endoscope into the patient comprises monitoring a rate of change of a camera exposure index to identify a point in time in which the endoscope is removed from the patient.

10. The system of claim 9, wherein the operation of monitoring the rate of change of the camera exposure index comprises monitoring a rate of change of a camera exposure index formed from a combination of exposure time and signal gain.

11. The system of claim 9, wherein the operations further comprise receiving indication of still image capture events within the camera and ignoring the camera exposure index associated with the camera during still image capture events to prevent false identification of removal of the endoscope from the patient.

12. A method for determining elapsed time for a surgical procedure conducted using an endoscope, comprising:
determining an insertion time of the endoscope into a patient via monitoring camera parameters of a camera that is positioned within the endoscope to identify the insertion time of the endoscope into the patient;
determining a removal time of the endoscope from the patient via monitoring camera parameters to identify the removal time of the endoscope from the patient;
generating an elapsed surgery time based upon the insertion time of the endoscope into the patient and the removal time of the endoscope from the patient; and
wherein monitoring camera parameters to identify the insertion time of the endoscope into the patient comprises monitoring a rate of change of a camera exposure index to identify a point in time in which the endoscope is inserted into the patient.

13. The method of claim 12, wherein monitoring the rate of change of the camera exposure index comprises monitoring a rate of change of a camera exposure index formed from a combination of exposure time and signal gain.

14. The method of claim 12, further comprising receiving indication of still image capture events within the camera and ignoring a camera exposure index associated with the camera during still image capture events to prevent false identification of insertion of the endoscope from the patient.

15. A method for determining elapsed time for a surgical procedure conducted using an endoscope, comprising:
determining an insertion time of the endoscope into a patient via monitoring camera parameters of a camera that is positioned within the endoscope to identify the insertion time of the endoscope into the patient;
determining a removal time of the endoscope from a patient via monitoring camera parameters to identify the removal time of the endoscope from the patient;
generating an elapsed surgery time based upon the insertion time of the endoscope into the patient and the removal time of the endoscope from the patient; and
wherein monitoring camera parameters to identify the removal time of the endoscope into the patient comprises monitoring a rate of change of a camera exposure index to identify a point in time in which the endoscope is removed from the patient.

16. The method of claim 15, wherein monitoring the rate of change of the camera exposure index comprises monitoring a rate of change of a camera exposure index formed from a combination of exposure time and signal gain.

17. The method of claim 15, further comprising receiving indication of still image capture events within the camera and ignoring the camera exposure index associated with the camera during still image capture events to prevent false identification of removal of the endoscope from the patient.

18. A non-transitory computer-readable device comprising instructions, which when loaded and executed by a processor, cause the processor to perform operations comprising:
determining an insertion time of an endoscope into a patient via monitoring camera parameters of the camera that is positioned within the endoscope to identify the insertion time of the endoscope into the patient;
determining a removal time of the endoscope from the patient via monitoring camera parameters to identify the removal time of the endoscope from the patient;
generating an elapsed surgery time based upon the insertion time of the endoscope into the patient and the removal time of the endoscope from the patient; and
wherein monitoring camera parameters to identify the insertion time of the endoscope into the patient comprises monitoring a rate of change of a camera exposure index to identify a point in time in which the endoscope is inserted into the patient.

* * * * *